(12) United States Patent
Yokozawa et al.

(10) Patent No.: US 6,984,738 B2
(45) Date of Patent: Jan. 10, 2006

(54) PROCESS FOR PRODUCTION OF OPTICALLY ACTIVE AMINO ALCOHOLS

(76) Inventors: Tohru Yokozawa, 4-7, Kameino 2-chome, Fujisawa-shi, Kanagawa 252-0813 (JP); Kenji Yagi, 9-13, Kamata 2-chome, Ohta-ku, Tokyo 144-0052 (JP); Takao Saito, 8-15, Yaguchi 3-chome, Ohta-ku, Tokyo 146-0093 (JP)

( * ) Notice: Subject to any disclaimer, the term of this patent is extended or adjusted under 35 U.S.C. 154(b) by 135 days.

(21) Appl. No.: 10/686,598

(22) Filed: Oct. 17, 2003

(65) Prior Publication Data

US 2004/0082794 A1 Apr. 29, 2004

(30) Foreign Application Priority Data

Oct. 18, 2002 (JP) .............................. 2002-305147

(51) Int. Cl.
 C07D 333/12 (2006.01)
 C07D 333/20 (2006.01)
 C07D 211/70 (2006.01)
 C07D 213/24 (2006.01)
 C07C 211/01 (2006.01)

(52) U.S. Cl. ........................ 549/75; 549/491; 546/334; 564/337; 564/357; 564/358

(58) Field of Classification Search ................ 564/337, 564/357, 358; 549/75, 491; 546/334
 See application file for complete search history.

(56) References Cited

U.S. PATENT DOCUMENTS

| 4,454,332 A | 6/1984 | Liu et al. ....................... 560/39 |
| 5,491,253 A | 2/1996 | Stuk et al. ..................... 560/27 |
| 5,672,706 A | 9/1997 | Haight et al. .................. 546/99 |

FOREIGN PATENT DOCUMENTS

| EP | 1 254 885 | 11/2002 |
| GB | 2 163 160 | 2/1986 |
| JP | 61-246176 | 11/1986 |
| JP | 11-189600 | 7/1999 |
| WO | 01/58843 | 8/2001 |

OTHER PUBLICATIONS

Matasumura et al., Journal of the American Chemical Society (1983), vol. 105, No. 20, p. 6312-6314.*
V. Jager et al., "Model Reactions for the Stereo-Controlled Synthesis of Aminopolyols; Reduction of Isoxazolines with Free or Protected Hydroxy Groups in Position 4 or in Side Chains", Angew. Chem. Int. Ed. Engl., vol. 20, No. 6/7, 1981, pp. 601-603.

(Continued)

*Primary Examiner*—Brian Davis

(74) *Attorney, Agent, or Firm*—Wenderoth, Lind & Ponack, L.L.P.

(57) ABSTRACT

The present invention is to provide a process for producing an optically active amino alcohol which is useful for the synthesis of natural substances and as an intermediate for drugs and agricultural chemicals in a high yield, a high selectivity and an economical manner with a good working efficiency and the present invention relates to a process for producing an optically active amino alcohol represented by the following formula (2)

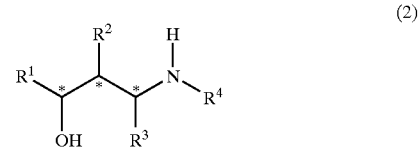

(2)

(in the formula, $R^1$ is a hydrocarbon group, a substituted hydrocarbon group, an aromatic heterocyclic group, a substituted aromatic heterocyclic group, an aliphatic heterocyclic group or a substituted aliphatic heterocyclic group; $R^2$ and $R^3$ each independently is hydrogen atom, a hydrocarbon group, a substituted hydrocarbon group, an acyl group, an acyloxy group, an alkyloxycarbonyl group, an aralkyloxycarbonyl group, an aryloxycarbonyl group, an aromatic heterocyclic group, a substituted aromatic heterocyclic group, an aliphatic heterocyclic group or a substituted aliphatic heterocyclic group; $R^4$ is hydrogen atom or a protective group; two or more of $R^1$, $R^2$, $R^3$ and $R^4$ may be bonded each other to form a ring; and * is asymmetric carbon) or a salt thereof which comprises subjecting a compound represented by the following formula (1) or a salt thereof to an asymmetric hydrogenation.

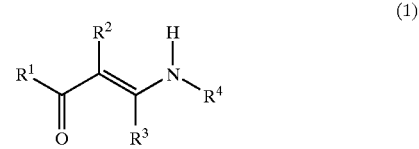

(1)

(in the formula, $R^1$ is a hydrocarbon group, a substituted hydrocarbon group, an aromatic heterocyclic group, a substituted aromatic heterocyclic group, an aliphatic heterocyclic group or a substituted aliphatic heterocyclic group; $R^2$ and $R^3$ each independently is hydrogen atom, a hydrocarbon group, a substituted hydrocarbon group, an acyl group, an acyloxy group, an alkyloxycarbonyl group, an aralkyloxycarbonyl group, an aryloxycarbonyl group, an aromatic heterocyclic group, a substituted aromatic heterocyclic group, an aliphatic heterocyclic group or a substituted aliphatic heterocyclic group; $R^4$ is hydrogen atom or a protective group; two or more of $R^1$, $R^2$, $R^3$ and $R^4$ may be bonded each other to form a ring; and a double bond is either cis or trans).

10 Claims, No Drawings

OTHER PUBLICATIONS

D. G. Melillo et al., "A Practical Synthesis of (±)-Thienamycin", Tetrahedron Letters, vol. 21, 1980, pp. 2783-2786.

T. L. Stuk et al., "An Efficient Stereocontrolled Strategy for the Synthesis of Hydroxyethylene Dipeptide Isosteres", J. Org. Chem., vol. 59, 1994, pp. 4040-4041.

G. Lunn, "Reduction of Heterocycles with Nickle-Aluminum Alloy", J. Org. Chem., vol. 52, 1987, pp. 1043-1046.

J. Barluenga et al., "Diasteroselective Synthesis of γ-Amino Alcohols with Three Chiral Centers by Reduction of β-Amino Ketones and Derivatives", J. Org. Chem., vol. 50, 1985, pp. 4052-4056.

V. J. Buchi et al., Helv. Chim. Acta, vol. 45, 1962, pp. 729-737.

M. G. Andrews et al., "Synthesis of β-Diamines and β-Amino Alcohols from a, β-Unsaturated Ketones and Aldehyde, Methylamine, and Borohydride Reducing Agents", J. Org. Chem., vol. 42, no. 4, 1977, pp. 650-652.

J. A. Meschino et al., "2-Amino-5,6-dihydro-1,3-oxazines. The Reduction of Carboxylic Esters with Sodium Borohydride", J. Org. Chem., vol. 28, Nov. 1963, pp. 3129-3134.

D. Ma et al., "A Simple and Stereospecific Route to 2,6-Disubstituted 4-Hydroxypiperidines. Synthesis of Dendrobate Alkaloid (+)-241D and formal Synthesis of (−)-Indolizidine 167B", Organic LEtters, vol. 2, No. 16, pp. 2503-2505, 2000.

Database, Chemical Abstracts, T. Ikariya et al., "Preparation of Ruthenium-Phosphine-Amine Complexes and Stereoselective Hydrogenation of Carbonyl Compounds to Optically Active Alcohols using the Complexes", Accession No. 131:87713 XP002265269. (1999).

* cited by examiner

PROCESS FOR PRODUCTION OF OPTICALLY ACTIVE AMINO ALCOHOLS

BACKGROUND OF THE INVENTION

1. Field of the Invention

The present invention relates to a process for the production of an optically active amino alcohol which is useful for synthesis of natural products and is useful as intermediates for drugs and agricultural chemicals.

2. Description of the Related Art

Optically active amino alcohols are the compounds which are not only useful for synthesis of natural products (Non-patent document 1) but also very useful as intermediates for drugs and agricultural chemicals (Patent Document 1, Patent Document 2, Non-patent Document 2 and Non-patent document 3).

Those optically active amino alcohols are able to be synthesized by i) reduction of keto-enamines (Patent Document 3), ii) reduction of isoxazolines and isoxazoles (Non-patent Document 4), iii) reduction of β-aminocarbonyl compounds (Non-patent Document 5), iv) reduction of ketopyridines (Non-patent Document 6), v) reduction of α,β-unsaturated ketones (Non-patent Document 7), vi) reduction of α-cyano esters (Non-patent Document 8), etc.

Methods mentioned in i) to vi) may be expressed by the following reaction formulae.

i) Reduction of keto-emanines

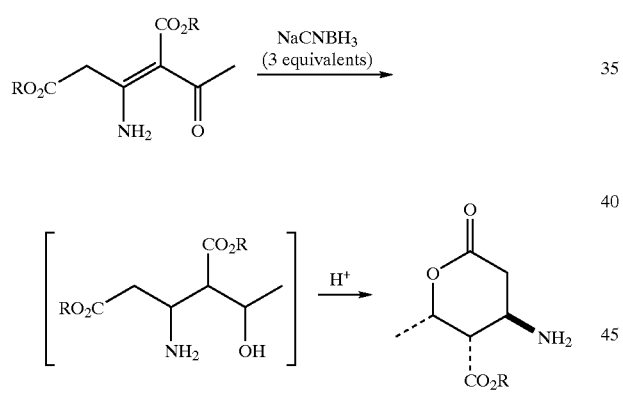

ii) Reduction of isoxazolines and isoxazoles

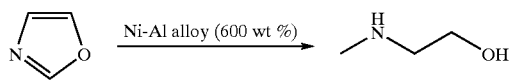

iii) Reduction of β-aminocarbonyl compounds

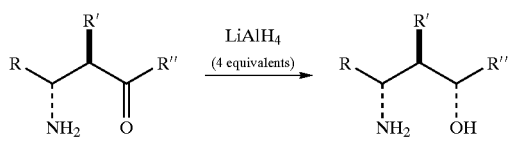

iv) Reduction of ketopyridines

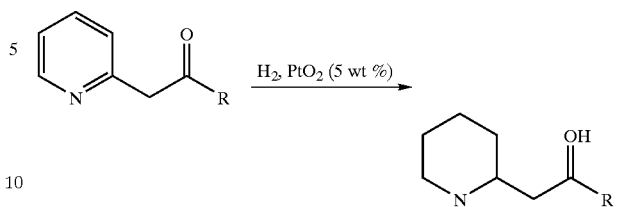

v) Reduction of α,β-unsaturated ketones

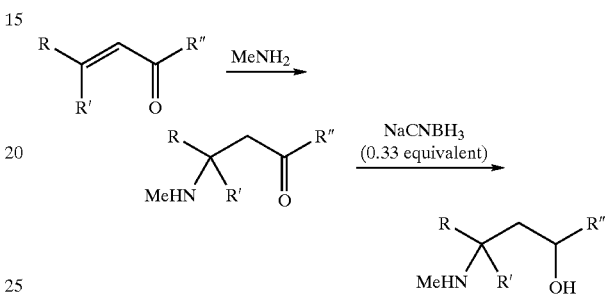

vi) Reduction of α-cyano esters

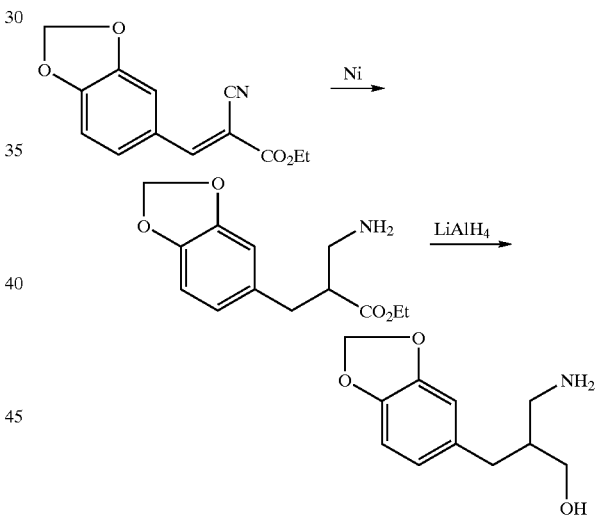

In the above reaction formulae, i) to iii) are carried out using the reagent such as lithium aluminum hydride (LiAlH$_4$), sodium cyanoborohydride (NaCNBH$_3$) or nickel-aluminum alloy (Ni—Al alloy) in an equivalent or more amount to the substrate. In addition, the reagent used is hard to handle and is used in an equivalent or more amount to the substrate and, therefore, excessive amount of the reagent is to be treated during the after-treatment whereby there is a problem that the working efficiency is bad. Therefore, the methods of i) to iii) contain the step which is believed to be a burden in conducting in an industrial scale and with economy.

In the meanwhile, methods where the reduction reaction is carried out by way of catalytic reaction are reported in iv) to vi) for solving the above problem. However, the methods mentioned in iv) to vi) have a problem that the product is a racemate.

3

Accordingly, there has been demanded a method where an optically active amino alcohol is synthesized at a low cost, with a good working efficiency, in an industrially applicable manner and in high yield and high selectivity.

Patent Document 1: U.S. Pat. No. 005,491,253 A
Patent Document 2: U.S. Pat. No. 4,454,332
Patent Document 3: JP 61/246176 A
Non-patent Document 1: *Angew. Chem., Int. Ed.*, 1981, 20, 601
Non-patent Document 2: *Tetrahedron Lett.*, 1980, 2783
Non-patent Document 3: *J. Org. Chem.*, 1994, 59, 4040
Non-patent Document 4: *J. Org. Chem.*, 1987, 52, 1043
Non-patent Document 5: *J. Org. Chem.*, 1985, 50, 4052
Non-patent Document 6: *Helv. Chim. Acta*, 1962, 45, 729
Non-patent Document 7: *J. Org. Chem.*, 1977, 42, 650
Non-patent Document 8: *J. Org. Chem.*, 1963, 28, 3129

SUMMARY OF THE INVENTION

The present invention has been achieved in view of the above-mentioned problems and its object is to provide a process for the production of an optically active amino alcohol in a high yield, a high selectivity and an economical manner with a good working efficiency.

The present inventors have carried out intensive investigations for a process for the production of an optically active amino alcohol which is useful for the synthesis of natural products and useful as an intermediate for drugs and agricultural chemicals. As a result, they have found that, when a keto-enamine represented by the formula (1) which will be mentioned later is subjected to an asymmetric hydrogenation reaction, carbonyl group and olefin existing in its molecule are reduced by a single step at the same time whereby the aimed optically active amino alcohol is able to be produced in a high yield and a high selectivity and, as a result of further investigations, the present invention has been achieved.

Thus, the present invention is as follows.

[1] A process for producing an optically active amino alcohol represented by the following formula (2)

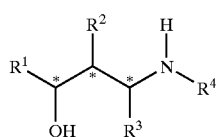

(2)

(in the formula, $R^1$ is a hydrocarbon group, a substituted hydrocarbon group, an aromatic heterocyclic group, a substituted aromatic heterocyclic group, an aliphatic heterocyclic group or a substituted aliphatic heterocyclic group; $R^2$ and $R^3$ each independently is hydrogen atom, a hydrocarbon group, a substituted hydrocarbon group, an acyl group, an acyloxy group, an alkyloxycarbonyl group, an aralkyloxycarbonyl group, an aryloxycarbonyl group, an aromatic heterocyclic group, a substituted aromatic heterocyclic group, an aliphatic heterocyclic group or a substituted aliphatic heterocyclic group; $R^4$ is hydrogen atom or a protective group; two or more of $R^1$, $R^2$, $R^3$ and $R^4$ may be bonded to each other to form a ring; and * is asymmetric carbon) or a salt thereof, which comprises subjecting a compound represented by the following formula (1) or a salt thereof to an asymmetric hydrogenation reaction.

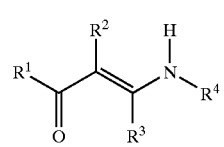

(1)

(in the formula, $R^1$ is a hydrocarbon group, a substituted hydrocarbon group, an aromatic heterocyclic group, a substituted aromatic heterocyclic group, an aliphatic heterocyclic group or a substituted aliphatic heterocyclic group; $R^2$ and $R^3$ each independently is hydrogen atom, a hydrocarbon group, a substituted hydrocarbon group, an acyl group, an acyloxy group, an alkyloxycarbonyl group, an aralkyloxycarbonyl group, an aryloxycarbonyl group, an aromatic heterocyclic group, a substituted aromatic heterocyclic group, an aliphatic heterocyclic group or a substituted aliphatic heterocyclic group; $R^4$ is hydrogen atom or a protective group; two or more of $R^1$, $R^2$, $R^3$ and $R^4$ may be bonded to each other to form a ring; and a double bond is either cis or trans).

[2] The process according to the above [1], wherein the asymmetric hydrogenation reaction is carried out in the presence of an asymmetric metal complex.

[3] The process according to the above [1], wherein the asymmetric hydrogenation reaction is carried out in the presence of a base.

[4] The process according to the above [3], wherein the amount of the base used is 0.15 to 10 equivalents relative to the compound represented by the formula (1).

DETAILED DESCRIPTION OF THE PREFERRED EMBODIMENTS

In the formulae (1) and (2), examples of the hydrocarbon group represented by $R^1$, $R^2$ and $R^3$ are an alkyl group, a cycloalkyl group, an alkenyl group, an alkynyl group, an aryl group and an aralkyl group. Examples of the substituted hydrocarbon group are a substituted alkyl group, a substituted cycloalkyl group, a substituted alkenyl group, a substituted alkynyl group, a substituted aryl group and a substituted aralkyl group.

The alkyl group may be either a straight or branched chain and, for example, it is an alkyl group having 1 to 8 carbon atoms. Specific examples of the alkyl group include methyl group, ethyl group, n-propyl group, 2-propyl group, n-butyl group, 2-butyl group, isobutyl group, tert-butyl group, n-pentyl group, 2-pentyl group, tert-pentyl group, 2-methylbutyl group, 3-methylbutyl group, 2,2-dimethylpropyl group, n-hexyl group, 2-hexyl group, 3-hexyl group, tert-hexyl group, 2-methylpentyl group, 3-methylpentyl group, 4-methylpentyl group, 5-methylpentyl group, n-heptyl group, 5-methylhexyl group, n-octyl group and 2-ethylhexyl group.

With regard to the substituted alkyl group, there is exemplified an alkyl group where at least one hydrogen atom of the above alkyl group is substituted with a substituent such as an alkoxy group or halogen atom.

The alkoxy group may be either a straight or branched chain and, for example, it is an alkoxy group having 1 to 6 carbon atoms. Specific examples of the alkoxy group include methoxy group, ethoxy group, n-propoxy group, 2-propoxy group, n-butoxy group, 2-butoxy group, isobutoxy group, tert-butoxy group, n-pentyloxy group, 2-methylbutoxy group, 3-methylbutoxy group, 2,2-dimethylpropyloxy group, n-hexyloxy group, 2-methylpentyloxy group, 3-methylpentyloxy group, 4-methylpentyloxy group, 5-methylpentyloxy group and cyclohexyloxy group. With regard to the halogen atom, there are exemplified fluorine atom, chlorine atom, bromine atom and iodine atom.

Specific examples of the alkyl group substituted with an alkoxy group, i.e. an alkoxyalkyl group, include methoxymethyl group, ethoxyethyl group and 2-butoxyethyl group. Specific examples of the alkyl group substituted with halogen atom(s), i.e. a halogenated alkyl group, include chloromethyl group, bromomethyl group, trifluoromethyl group, 2,2,2-trichloroethyl group, 3-chloropropyl group and 3,3,3-trifluoropropyl group.

The alkenyl group may be either a straight or branched chain and it is, for example, an alkenyl group having 2 to 8 carbon atoms. Specific examples of the alkenyl group include ethenyl group, propenyl group, butenyl group, pentenyl group, hexenyl group, heptenyl group and octenyl group.

With regard to the substituted alkenyl group, there is exemplified an alkenyl group where at least one hydrogen atom in the above alkenyl group is substituted with a substituent such as an alkoxy group or halogen atom.

The alkynyl group may be either a straight or branched chain and it is, for example, an alkynyl group having 2 to 8 carbon atoms. Specific examples of the alkynyl group include ethynyl group, 2-propynyl group, 3-butynyl group, 4-pentynyl group and 7-octynyl group.

With regard to the substituted alkynyl group, there is exemplified an alkynyl group where at least one hydrogen atom in the above alkynyl group is substituted with a substituent such as an alkoxy group or halogen atom.

With regard to the aryl group, there is exemplified an aryl group having 6 to 14 carbon atoms. Specific examples of the aryl group include phenyl group, naphthyl group and anthryl group.

With regard to the substituted aryl group, there is exemplified an aryl group where at least one hydrogen atom of the above aryl group is substituted with a substituent such as an alkyl group, an alkoxy group, halogen atom, nitro group or cyano group. The alkyl group may be either a straight or branched chain and its example is an alkyl group having 1 to 4 carbon atoms. Specific examples of the alkyl group include methyl group, ethyl group, n-propyl group, 2-propyl group, n-butyl group, 2-butyl group, isobutyl group and tert-butyl group. The alkoxy group may be either a straight or branched chain and its example is an alkoxy group having 1 to 4 carbon atoms. Specific examples of the alkoxy group include methoxy group, ethoxy group, n-propoxy group, 2-propoxy group, n-butoxy group, 2-butoxy group, isobutoxy group and tert-butoxy group. Examples of the halogen atom are fluorine atom, chlorine atom, bromine atom and iodine atom. Specific examples of the substituted aryl group include 4-methoxyphenyl group, 3,5-dimethoxyphenyl group, 4-chlorophenyl group and 4-nitrophenyl group.

With regard to the cycloalkyl group, there is exemplified a cycloalkyl group having 3 to 8 carbon atoms. Specific examples of the cycloalkyl group include cyclopropyl group, cyclobutyl group, cyclopentyl group, cyclohexyl group, cycloheptyl group, 2-methylcyclopentyl group, 3-methylcyclopentyl group, cycloheptyl group, 2-methylcyclohexyl group, 3-methylcyclohexyl group and 4-methylcyclohexyl group.

With regard to the substituted cycloalkyl group, there is exemplified a cycloalkyl group where at least one hydrogen atom of the above cycloalkyl group is substituted with a substituent such as an alkyl group, an alkoxy group, halogen atom, nitro group or cyano group. The alkyl group may be either a straight or branched chain and there is exemplified an alkyl group having 1 to 4 carbon atoms. Specific examples of the alkyl group include methyl group, ethyl group, n-propyl group, 2-propyl group, n-butyl group, 2-butyl group, sec-butyl group and tert-butyl group. The alkoxy group may be either a straight or branched chain and there is exemplified an alkoxy group having 1 to 4 carbon atoms. Specific examples of the alkoxy group include methoxy group, ethoxy group, n-propoxy group, 2-propoxy group, n-butoxy group, sec-butoxy group and tert-butoxy group. With regard to the halogen atom, there are exemplified fluorine atom, chlorine atom, bromine atom and iodine atom. Specific examples of the substituted cycloalkyl group are a 4-methoxycycloalkyl group, a 3,5-dimethoxycycloalkyl group, a 4-chlorocycloalkyl group and a 4-nitrocycloalkyl group.

With regard to the aralkyl group, there is exemplified an aralkyl group having 7 to 14 carbon atoms. Specific examples of the aralkyl group include benzyl group, 2-phenylethyl group, 1-phenylpropyl group, 2-phenylpropyl group, 3-phenylpropyl group, 1-phenylbutyl group, 2-phenylbutyl group, 3-phenylbutyl group, 4-phenylbutyl group, 1-phenylpentyl group, 2-phenylpentyl group, 3-phenylpentyl group, 4-phenylpentyl group, 5-phenylpentyl group, 1-phenylhexyl group, 2-phenylhexyl group, 3-phenylhexyl group, 4-phenylhexyl group, 5-phenylhexyl group, 6-phenylhexyl group and 9-fluorenylmethyl group.

With regard to the substituted aralkyl group, there is exemplified an aralkyl group where at least one hydrogen atom is substituted with a substituent such as an alkyl group, an alkoxy group, halogen atom, nitro group or cyano group. The alkyl group may be either a straight or branched chain and there is exemplified an alkyl group having 1 to 4 carbon atoms. Specific examples of the alkyl group include methyl group, ethyl group, n-propyl group, 2-propyl group, n-butyl group, 2-butyl group, isobutyl group and tert-butyl group. The alkoxy group may be either a straight or branched chain and there is exemplified an alkoxy group having 1 to 4 carbon atoms. Specific examples of the alkoxy group include methoxy group, ethoxy group, n-propoxy group, 2-propoxy group, n-butoxy group, 2-butoxy group, isobutoxy group and tert-butoxy group. With regard to the halogen atom, there are exemplified fluorine atom, chlorine atom, bromine atom and iodine atom. Specific examples of the substituted aralkyl group include 4-methoxybenzyl group, 3,5-dimethoxybenzyl group, 4-chlorobenzyl group and 4-nitrobenzyl group.

With regard to the aromatic heterocyclic group represented by $R^1$, $R^2$ and $R^3$, a five- or six-membered monocyclic aromatic heterocyclic group or polycyclic aromatic heterocyclic group, for example, is preferred and there is exemplified an aromatic heterocyclic group having 4 to 14 carbon atoms containing 1 to 3 hetero atoms such as nitrogen atom(s), oxygen atom(s) and/or sulfur atom(s) as heterogeneous kind of atoms. Specific examples of the aromatic heterocyclic group include pyridyl group, imidazolyl group, thiazolyl group, furfuryl group, pyranyl group, furyl group, benzofuryl group and thienyl group.

With regard to the substituted aromatic heterocyclic group represented by $R^1$, $R^2$ and $R^3$, there is exemplified an aromatic heterocyclic group where at least one hydrogen atom in the above aromatic heterocyclic group is substituted with a substituent such as an alkyl group, a cycloalkyl group, a halogenated alkyl group, an alkoxy group and halogen atom. These substituents may be the same as those mentioned above.

With regard to the aliphatic heterocyclic group represented by $R^1$, $R^2$ and $R^3$, a five- or six-membered aliphatic heterocyclic group, for example, is preferred and there is exemplified an aliphatic heterocyclic group having 4 to 14 carbon atoms containing 1 to 3 hetero atoms such as nitrogen atom(s), oxygen atom(s) and/or sulfur atom(s) as heterogeneous kind of atoms. Specific examples of the aliphatic heterocyclic group include pyrrolidyl-2-one group, piperidino group, piperidino, piperazinyl group, morpholino group, morpholinyl group, tetrahydrofuryl group and tetrahydropyranyl group.

With regard to the substituted aliphatic heterocyclic group represented by $R^1$, $R^2$ and $R^3$, there is exemplified an aliphatic heterocyclic group where at least one hydrogen atom in the above aliphatic heterocyclic group is substituted with a substituent such as an alkyl group, a cycloalkyl group, a halogenated alkyl group, an alkoxy group and halogen atom. These substituents may be the same with those mentioned above.

The acyl group represented by $R^2$ and $R^3$ may be either a straight or branched chain or may be cyclic and there is exemplified an acyl group having, for example, 2 to 30 carbon atoms derived from a carboxylic acid. Specific examples of the acyl group include acetyl group, propionyl group, isopropionyl group, butyryl group, pentanoyl group, hexanoyl group, pivaloyl group, oleoyl group, cyclohexylcarbonyl group, acryloyl group, crotonoyl group, benzoyl group, naphthoyl group and nicotinoyl group. The acyl group may be an acyl group derived from a sulfonic acid or a phosphonic acid corresponding to the above acyl group derived from carboxylic acid.

The acyloxy group represented by $R^2$ and $R^3$ may be either a straight or branched chain or may be cyclic, and there is exemplified an acyloxy group having, for example, 2 to 30 carbon atoms derived from a carboxylic acid. Specific examples of the acyloxy group include acetyloxy group, propionyloxy group, isopropionyloxy group, butyryloxy group, pentanoyloxy group, hexanoyloxy group, pivaloyloxy group, oleoyloxy group, cyclohexylcarbonyloxy group, acryloyloxy group, crotonoyloxy group, benzoyloxy group, naphthoyloxy group and nicotinoyloxy group.

The alkyloxycarbonyl group represented by $R^2$ and $R^3$ may be either a straight or branched chain or may be cyclic and there is exemplified an alkyloxycarbonyl group having, for example, 2 to 30 carbon atoms. Specific examples of the alkyloxycarbonyl group include methoxycarbonyl group, ethoxycarbonyl group, propyloxycarbonyl group, isopropyloxycarbonyl group, tert-butyloxycarbonyl group and cyclohexyloxycarbonyl group.

The aralkyloxycarbonyl group represented by $R^2$ and $R^3$ may be either a straight or branched chain or may be cyclic and there is exemplified an aralkyloxycarbonyl group having, for example, 6 to 30 carbon atoms. Specific examples of the aralkyloxycarbonyl group include benzyloxycarbonyl group and 9-fluorenylmethyloxycarbonyl group.

With regard to the aryloxycarbonyl group represented by $R^2$ and $R^3$, there is exemplified an aryloxycarbonyl group having, for example, 6 to 30 carbon atoms. Specific examples of the aryloxycarbonyl group include phenoxycarbonyl group, etc.

With regard to a protective group represented by $R^4$, any group may be used so far as it is able to be used as a protective group for amino group and there are exemplified those which are mentioned as protective groups for amino group in "Protective Groups in Organic Synthesis, Second Edition (John Wiley & Sons, Inc. (1991))". Specific examples of the protective group for amino group are a hydrocarbon group, a substituted hydrocarbon group, an acyl group, an alkyloxycarbonyl group, an aralkyloxycarbonyl group and an aryloxycarbonyl group.

With regard to the hydrocarbon group, the substituted hydrocarbon group, the acyl group, the alkyloxycarbonyl group, the aralkyloxycarbonyl group and the aryloxycarbonyl group, they are as mentioned above.

With regard to $R^1$, $R^2$, $R^3$ and $R^4$, two or more thereof may be taken together to form a ring and, for example, two of the groups $R^1$, $R^2$, $R^3$ and $R^4$ may form, for example, an alkylene group having 1 to 6 carbon atoms such as methylene group, ethylene group and propylene group or an alkylenedioxy group having 1 to 6 carbon atoms such as methylenedioxy group, ethylenedioxy group, propylenedioxy group and trimethylenedioxy group.

Incidentally, when $R^2$ or $R^3$ in the formula (2) is hydrogen atom, the carbon atom to which $R^2$ or $R^3$ is bonded is not an asymmetric carbon.

Specific examples of the compound represented by the formula (1) used in the present invention include 3-methylamino-1-thiophen-2-yl-propenone, 3-methylamino-1-phenylpropenone and the compounds represented by the following formulae.

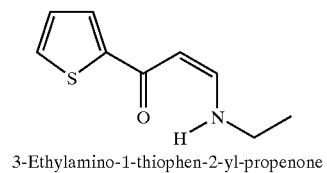

3-Ethylamino-1-thiophen-2-yl-propenone

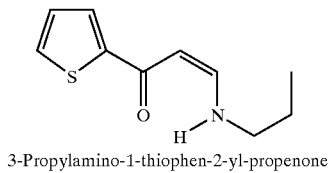

3-Propylamino-1-thiophen-2-yl-propenone

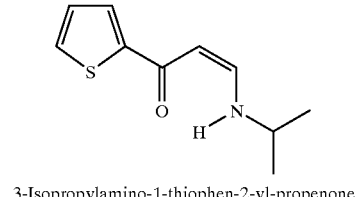

3-Isopropylamino-1-thiophen-2-yl-propenone

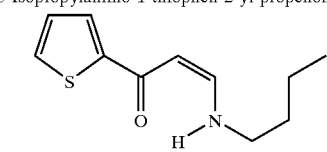

3-Butylamino-1-thiophen-2-yl-propenone

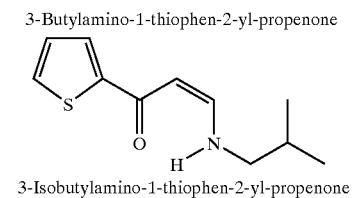

3-Isobutylamino-1-thiophen-2-yl-propenone

-continued

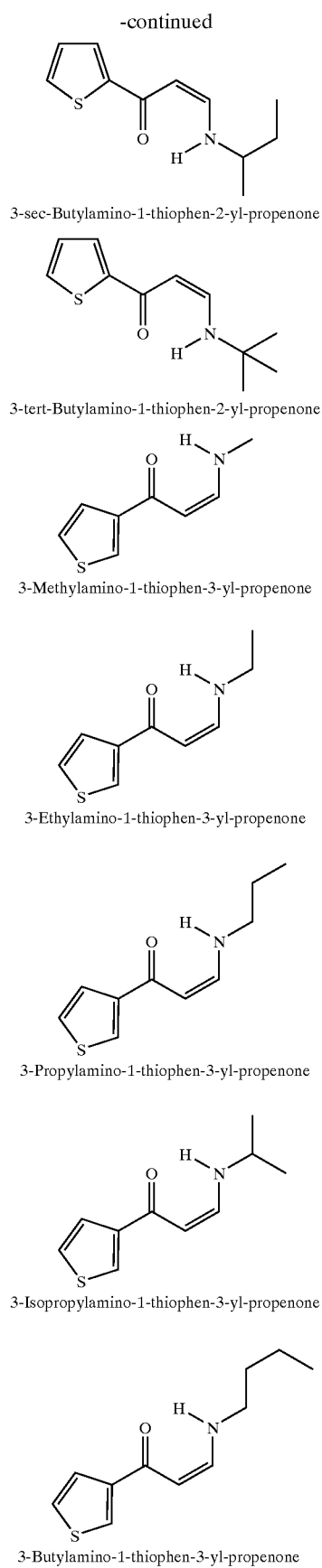

3-sec-Butylamino-1-thiophen-2-yl-propenone 3-tert-Butylamino-1-thiophen-2-yl-propenone 3-Methylamino-1-thiophen-3-yl-propenone 3-Ethylamino-1-thiophen-3-yl-propenone 3-Propylamino-1-thiophen-3-yl-propenone 3-Isopropylamino-1-thiophen-3-yl-propenone 3-Butylamino-1-thiophen-3-yl-propenone -continued

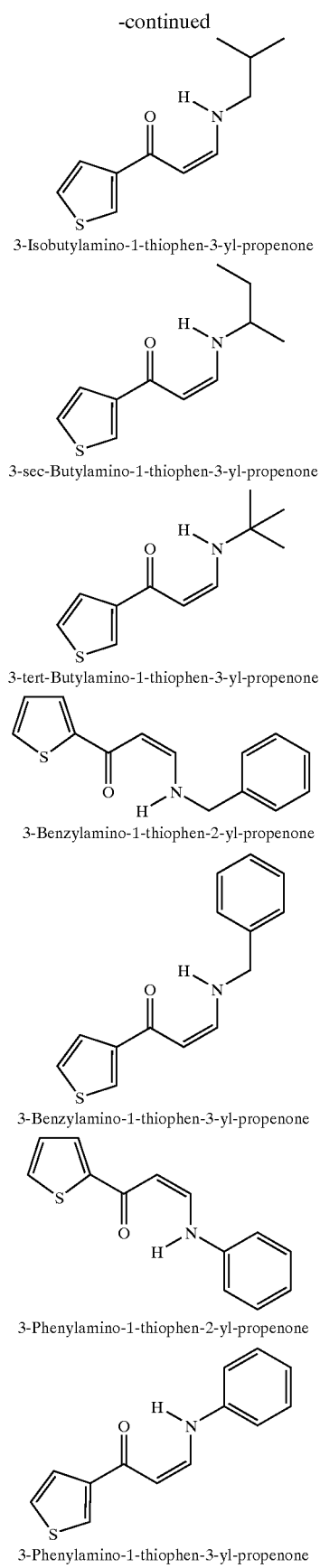

3-Isobutylamino-1-thiophen-3-yl-propenone 3-sec-Butylamino-1-thiophen-3-yl-propenone 3-tert-Butylamino-1-thiophen-3-yl-propenone 3-Benzylamino-1-thiophen-2-yl-propenone 3-Benzylamino-1-thiophen-3-yl-propenone 3-Phenylamino-1-thiophen-2-yl-propenone 3-Phenylamino-1-thiophen-3-yl-propenone

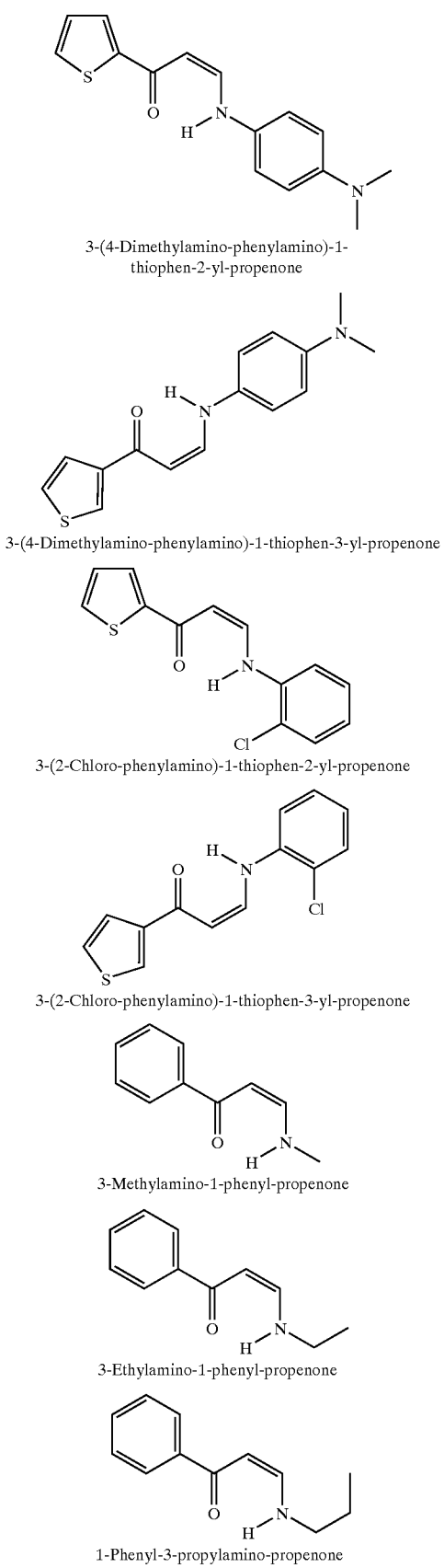
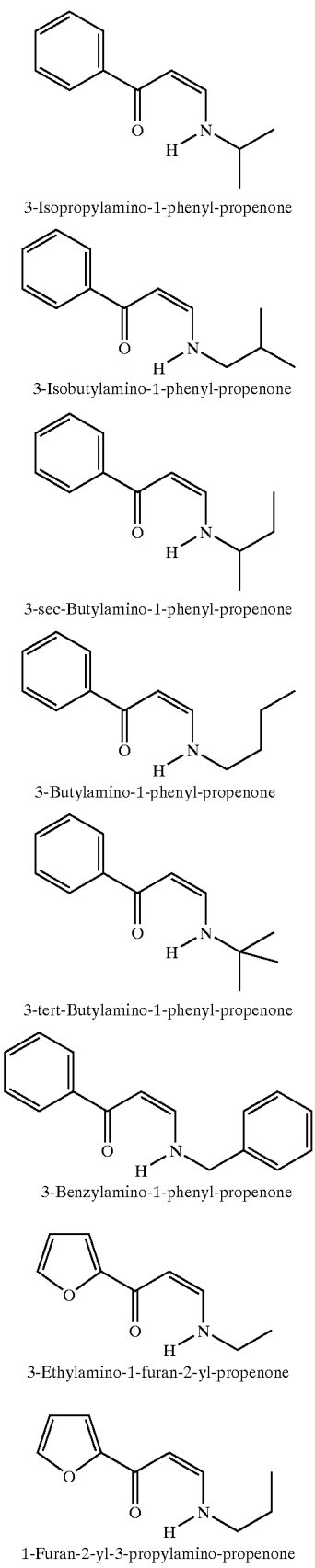

-continued

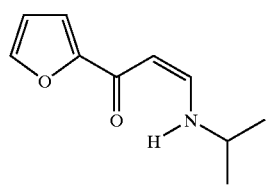
1-Furan-2-yl-3-isopropylamino-propenone

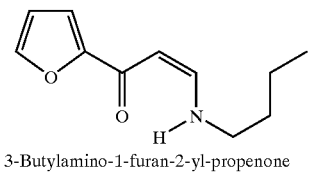
3-Butylamino-1-furan-2-yl-propenone

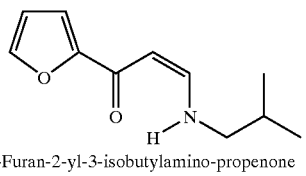
1-Furan-2-yl-3-isobutylamino-propenone

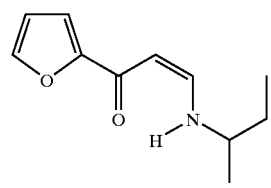
3-sec-Butylamino-1-furan-2-yl-propenone

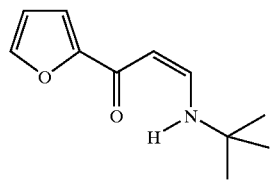
3-tert-Butylamino-1-furan-2-yl-propenone

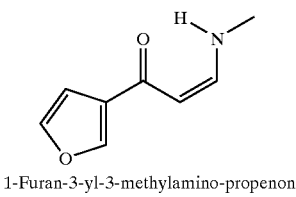
1-Furan-3-yl-3-methylamino-propenone

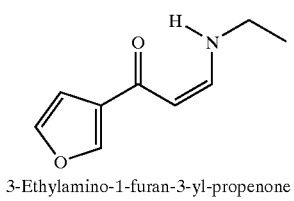
3-Ethylamino-1-furan-3-yl-propenone

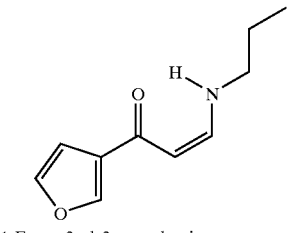
1-Furan-3-yl-3-propylamino-propenone

-continued

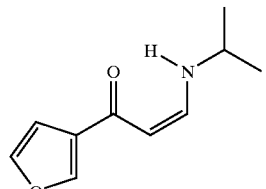
1-Furan-3-yl-3-isopropylamino-propenone

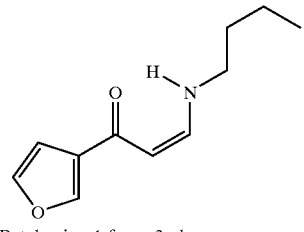
3-Butylamino-1-furan-3-yl-propenone

1-Furan-3-yl-3-isobutylamino-propenone

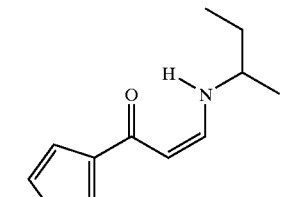
3-sec-Butylamino-1-furan-3-yl-propenone

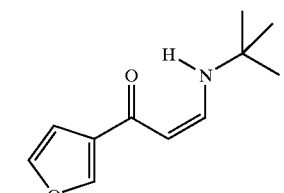
3-tert-Butylamino-1-furan-3-yl-propenone

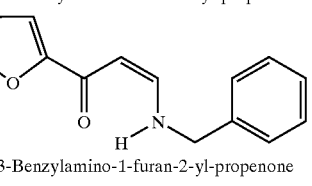
3-Benzylamino-1-furan-2-yl-propenone

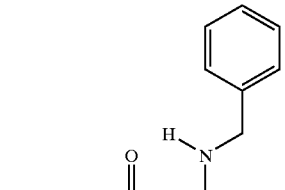
3-Benzylamino-1-thiophen-3-yl-propenone

-continued

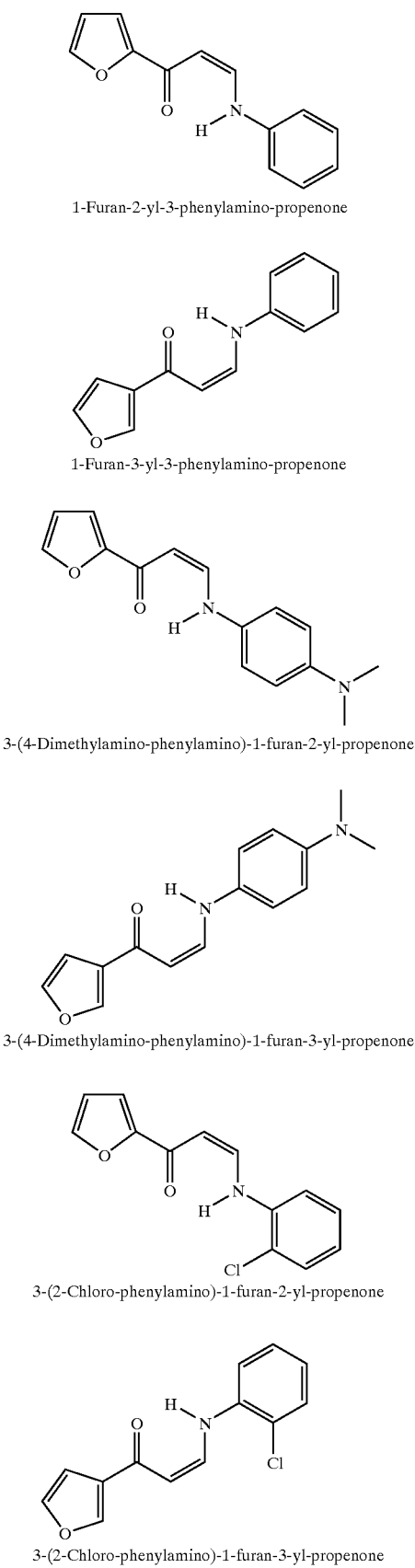

1-Furan-2-yl-3-phenylamino-propenone

1-Furan-3-yl-3-phenylamino-propenone 3-(4-Dimethylamino-phenylamino)-1-furan-2-yl-propenone 3-(4-Dimethylamino-phenylamino)-1-furan-3-yl-propenone 3-(2-Chloro-phenylamino)-1-furan-2-yl-propenone 3-(2-Chloro-phenylamino)-1-furan-3-yl-propenone -continued

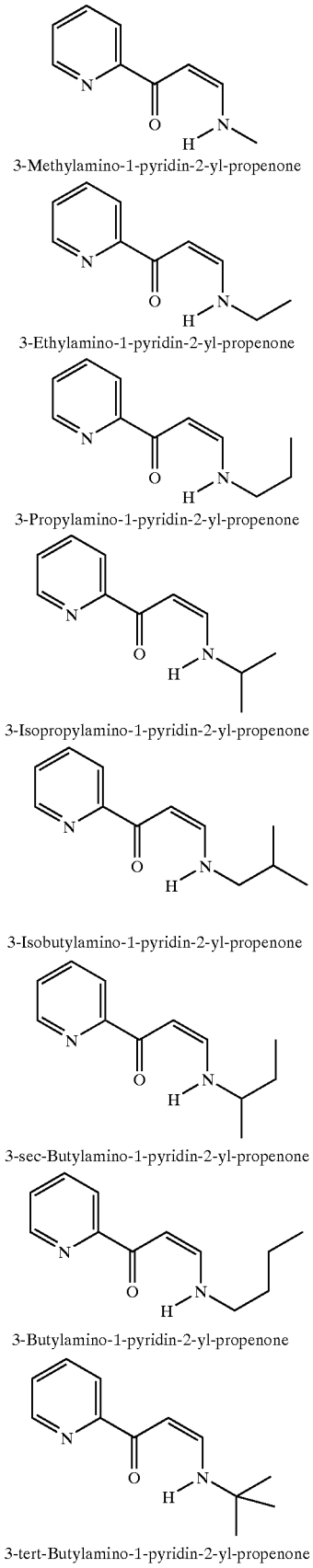

3-Methylamino-1-pyridin-2-yl-propenone

3-Ethylamino-1-pyridin-2-yl-propenone

3-Propylamino-1-pyridin-2-yl-propenone

3-Isopropylamino-1-pyridin-2-yl-propenone

3-Isobutylamino-1-pyridin-2-yl-propenone 3-sec-Butylamino-1-pyridin-2-yl-propenone 3-Butylamino-1-pyridin-2-yl-propenone 3-tert-Butylamino-1-pyridin-2-yl-propenone

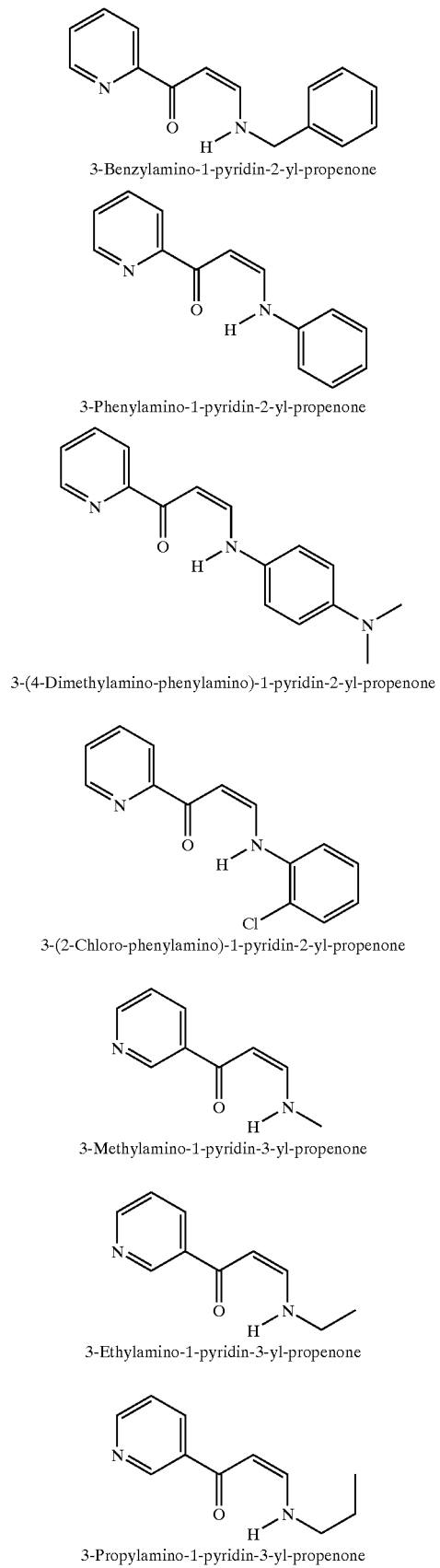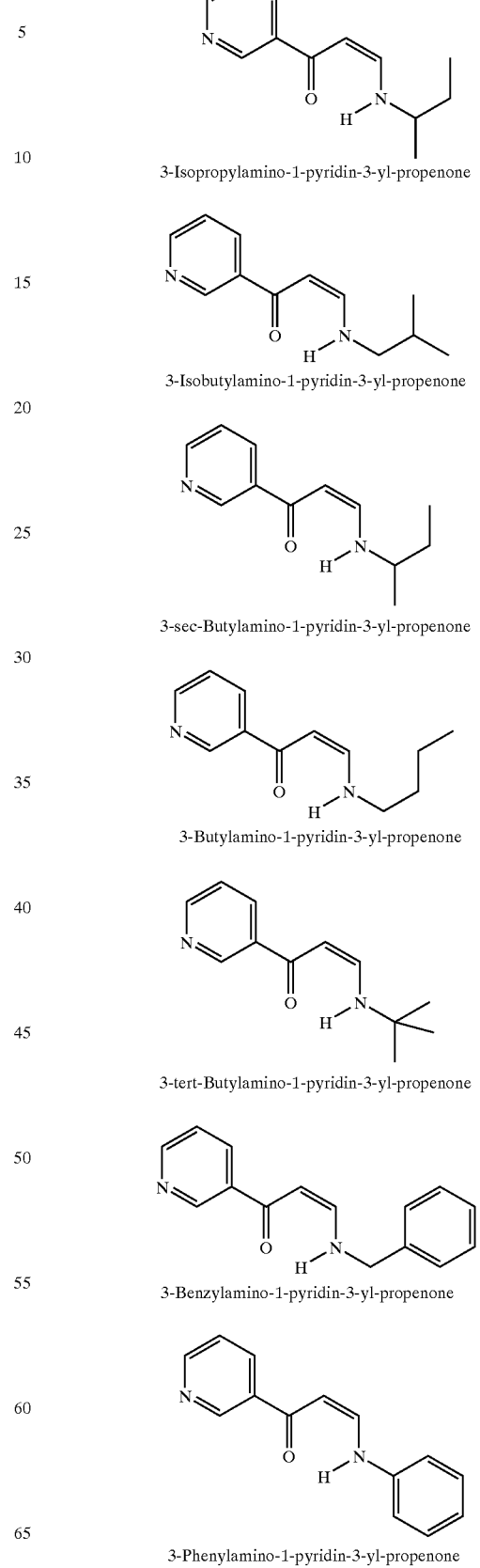

-continued

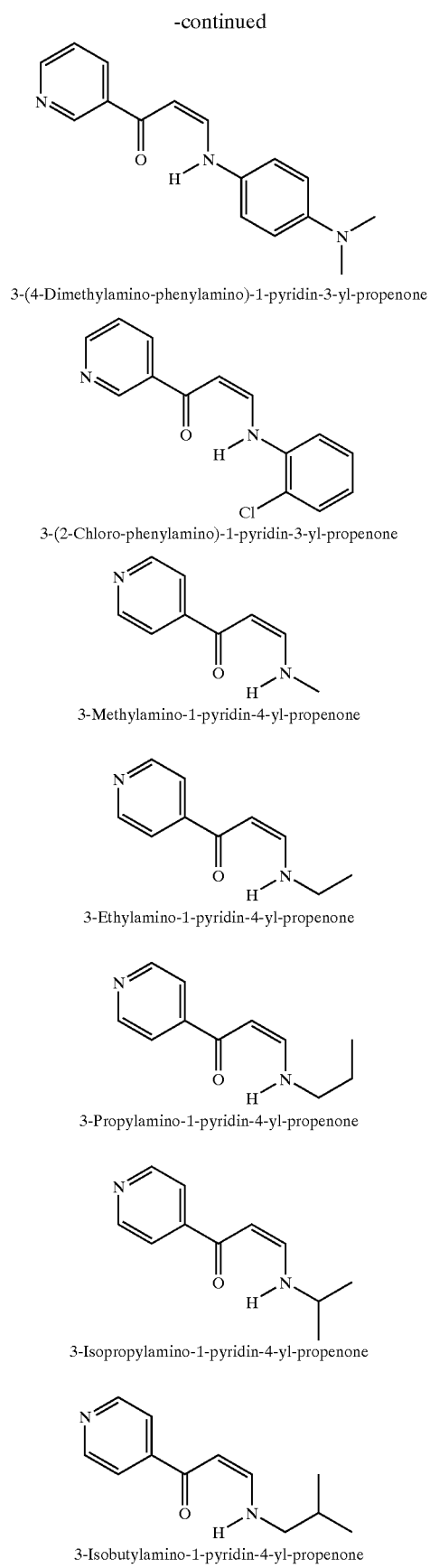

3-(4-Dimethylamino-phenylamino)-1-pyridin-3-yl-propenone 3-(2-Chloro-phenylamino)-1-pyridin-3-yl-propenone 3-Methylamino-1-pyridin-4-yl-propenone 3-Ethylamino-1-pyridin-4-yl-propenone 3-Propylamino-1-pyridin-4-yl-propenone 3-Isopropylamino-1-pyridin-4-yl-propenone 3-Isobutylamino-1-pyridin-4-yl-propenone -continued

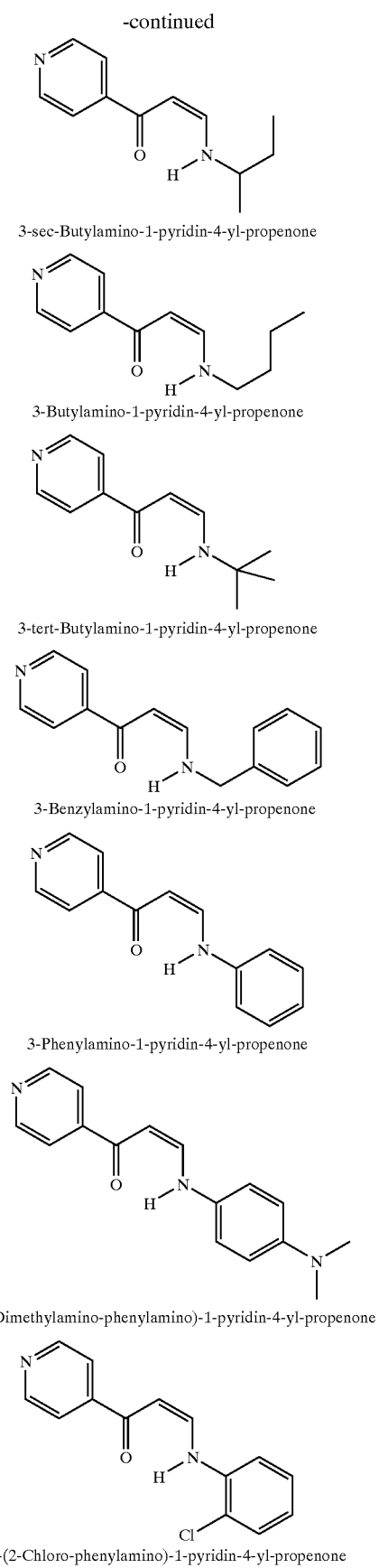

3-sec-Butylamino-1-pyridin-4-yl-propenone

3-Butylamino-1-pyridin-4-yl-propenone 3-tert-Butylamino-1-pyridin-4-yl-propenone 3-Benzylamino-1-pyridin-4-yl-propenone 3-Phenylamino-1-pyridin-4-yl-propenone 3-(4-Dimethylamino-phenylamino)-1-pyridin-4-yl-propenone 3-(2-Chloro-phenylamino)-1-pyridin-4-yl-propenone

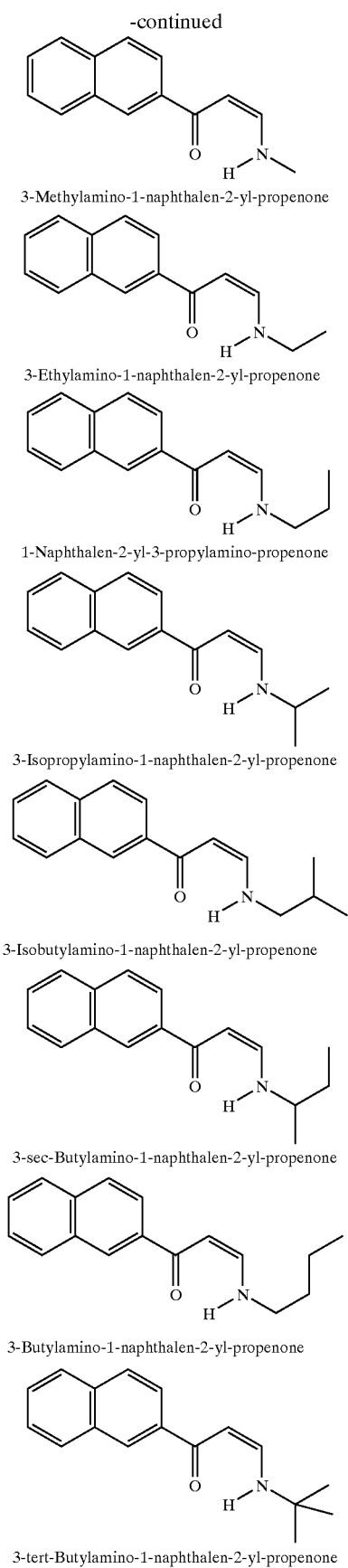
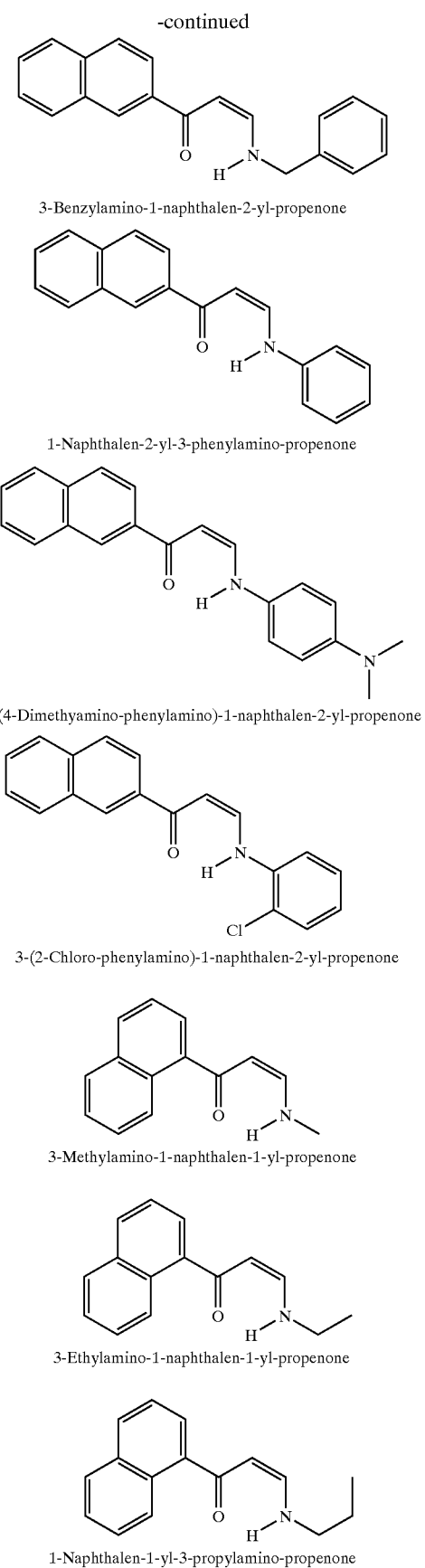

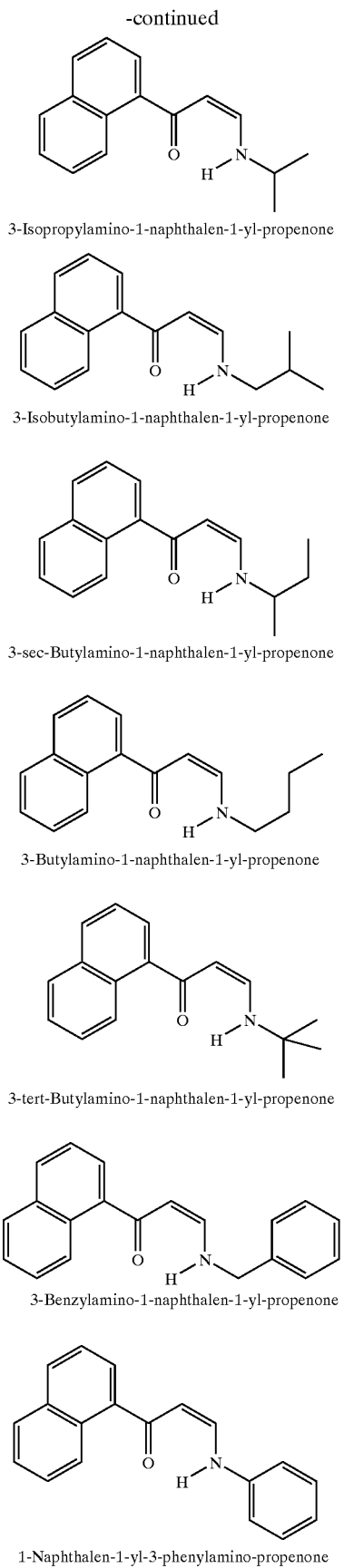

3-Isopropylamino-1-naphthalen-1-yl-propenone

3-Isobutylamino-1-naphthalen-1-yl-propenone 3-sec-Butylamino-1-naphthalen-1-yl-propenone 3-Butylamino-1-naphthalen-1-yl-propenone 3-tert-Butylamino-1-naphthalen-1-yl-propenone 3-Benzylamino-1-naphthalen-1-yl-propenone 1-Naphthalen-1-yl-3-phenylamino-propenone

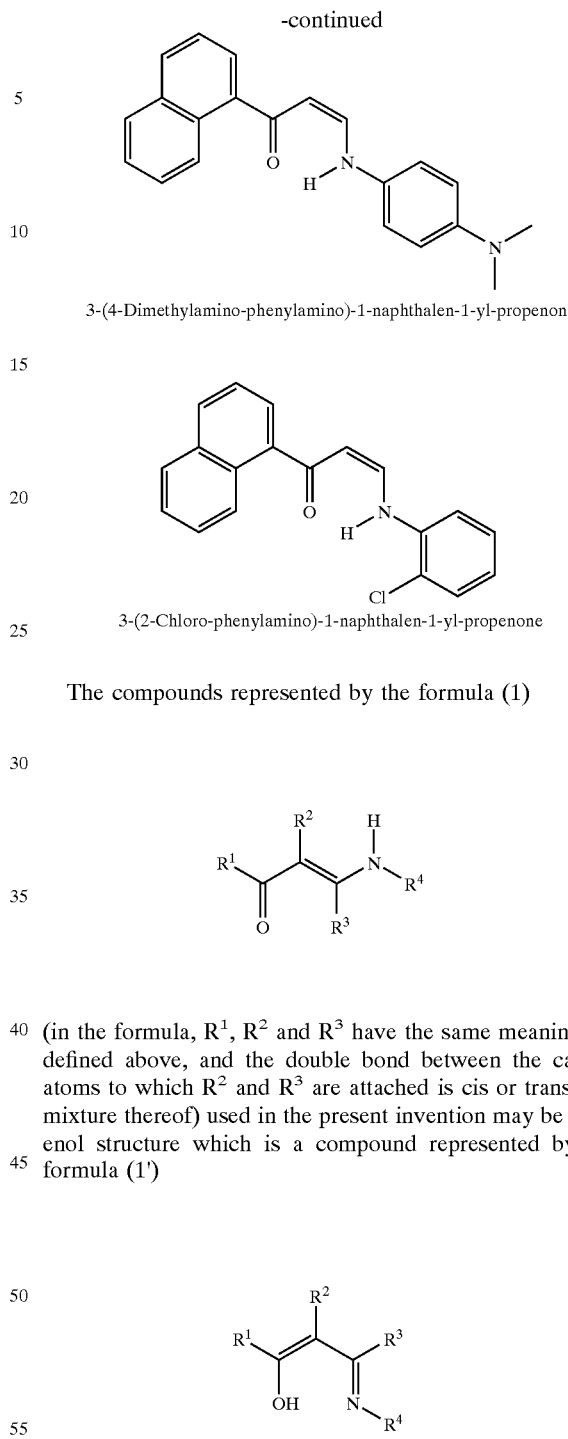

3-(4-Dimethylamino-phenylamino)-1-naphthalen-1-yl-propenone 3-(2-Chloro-phenylamino)-1-naphthalen-1-yl-propenone The compounds represented by the formula (1)

(1)

(in the formula, $R^1$, $R^2$ and $R^3$ have the same meanings as defined above, and the double bond between the carbon atoms to which $R^2$ and $R^3$ are attached is cis or trans or a mixture thereof) used in the present invention may be in an enol structure which is a compound represented by the formula (1')

(1')

(in the formula, $R^1$, $R^2$ and $R^3$ have the same meanings as defined above) in a reaction system or in an isolated state depending upon the type of the compound.

The both compounds (1) and (1') are in the relation of the keto-enol tautomerism, and it should be construed that each of the compounds represented by the formula (1) and the compound represented by the formula (2) as well as its mixture are substantially the same and they fall within the scope of the present invention.

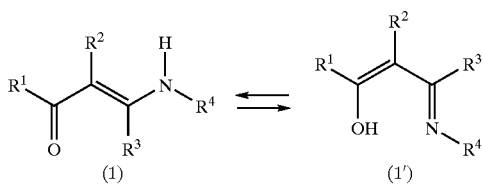

In other words, the compound represented by the above formula (1) used in the present invention also covers the compound represented by the above formula (1') as well as a mixture thereof within its scope.

In the process according to the present invention, an optically active amino alcohol represented by the formula (2) can be prepared in a high yield and a high optical purity by an asymmetric hydrogenation of the compound represented by the formula (1) and/or the formula (1') without protecting with a protective group but, when the compound represented by the formula (1) is in a structure represented by the formula (1') having a structure of an enol form, an optically active amino alcohol represented by the formula (2) can be prepared in a high yield and a high optical purity even when a protective group is introduced into hydroxyl group.

Accordingly, the process according to the present invention is to be understood to be able to give an optically active amino alcohol represented by the above formula (2) in a high yield and a high optical purity by an asymmetric hydrogenation of a compound represented by the above formula (1), a compound represented by the above formula (1') or a mixture of the compound represented by the above formula (1) and the compound represented by the above formula (1') (in other words, the compound represented by the above formula (1) and/or the compound represented by the above formula (1')).

Each of the compound represented by the formula (1), the compound represented by the formula (1') and the compound represented by the formula (2) may be in the form of a salt with an inorganic acid such as hydrochloric acid, sulfuric acid, nitric acid etc. or with an organic base such as dimethyl amine or triethyl amine etc. when the compound has an acidic group such as carboxyl or sulfo group etc.

The process according to the present invention is illustrated by way of the following reaction formulae using the form of a free base.

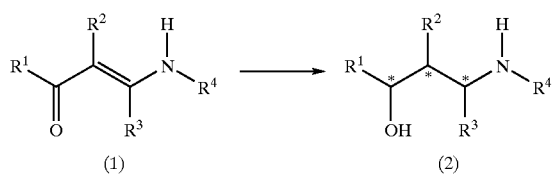

When a keto-enamine which is a compound represented by the formula (1) is subjected to an asymmetric hydrogenation using an asymmetric metal complex and hydrogen gas in the presence of a base if desired, an optically active amino alcohol represented by the formula (2) can be prepared. With regard to the asymmetric metal complex, an asymmetric metal complex mentioned, for example, in the Japanese Patent Laid-Open No. 11/189,600 A is able to be used.

Specific examples of the asymmetric metal complex include $RuCl_2[(R)\text{-binap}][(R,R)\text{-dpen}]$, $RuCl_2[(R)\text{-binap}][(R)\text{-daipen}]$, $RuCl_2[(R)\text{-Tol-binap}][(R,R)\text{-dpen}]$, $RuCl_2[(R)\text{-Tol-binap}][(R)\text{-daipen}]$, $RuCl_2[(R)\text{-DM-binap}][(R,R)\text{-dpen}]$ and $RuCl_2[(R)\text{-DM-binap}][(R)\text{-daipen}]$. With regard to the asymmetric metal complex, $RuCl_2[(R)\text{-DM-binap}][(R)\text{-daipen}]$, etc. may be used preferably. Here, BINAP means 2,2'-bis(diphenylphosphino)-1,1'-binaphthyl, Tol-BINAP means 2,2'-bis(di-p-tolylphosphino)-1,1'-binaphthyl, DM-BINAP means 2,2'-bis[bis(3,5-dimethylphenyl)phosphino]-1,1'-binaphthyl, DPEN means 1,2-diphenyl-ethylenediamine and DAIPEN means 1,1-di(4-anisyl)-2-isopropyl-1,2-ethylenediamine.

Amount of the compounds represented by formula (1), i.e. a keto-enamine (1) and the asymmetric metal complex used varies depending upon reactor, reaction system or economy. The amount of the asymmetric metal complex may be used in 1/10 to 1/100,000 in terms of a molar ratio to the above reaction substrate (a keto-enamine (1) such as 3-methylamino-1-thiophen-2-yl-propenone) or, preferably, may be used within a range of 1/50 to 1/10,000.

With regard to the base, there are exemplified an inorganic base and an organic base. Examples of the inorganic base include potassium carbonate ($K_2CO_3$), potassium hydroxide (KOH), lithium hydroxide (LiOH), sodium hydrogen carbonate ($NaHCO_3$), sodium carbonate ($Na_2CO_3$), potassium hydrogen carbonate ($KHCO_3$) and sodium hydroxide (NaOH). Examples of the organic base are salts of alkaline and alkaline earth metal such as potassium methoxide ($KOCH_3$), sodium methoxide ($NaOCH_3$), lithium methoxide ($LiOCH_3$), sodium ethoxide ($NaOCH_2CH_3$), potassium isopropoxide ($KOCH(CH_3)_2$), potassium tert-butoxide ($KOC(CH_3)_3$), lithium methoxide ($LiOCH_3$) and potassium naphthalenide ($KC_{10}H_8$); organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine and N-methylmorpholine. The base used in the present invention may be metal hydrides such as sodium hydride, sodium borohydride and lithium aluminum hydride; organometallic compounds such as methyl magnesium bromide, ethyl magnesium bromide, propyl magnesium bromide, methyl lithium, ethyl lithium, propyl lithium, n-butyl lithium and tert-butyl lithium; or quaternary ammonium salts. With regard to the base used in the present invention, it is not limited to the above-mentioned bases only so far as an amine-phosphine ruthenium hydride complex is generated thereby and hydrogen or the like is able to be used as well. Those bases may be used alone or as a mixture of two or more bases. Among those bases, the inorganic bases and the salts of alkaline and alkaline earth metals are particularly preferred.

Amount of the base used is 0.15 to 10 equivalents or, preferably, 0.2 to 2 equivalents to the compound represented by the above formula (1) which is a reaction substrate.

It is preferred that the asymmetric hydrogenation reaction is carried out in a solvent. Specific examples of the solvent include amides such as N,N-dimethylformamide (DMF), formamide and N,N-dimethylacetamide (DMA); cyano-containing compounds such as acetonitrile; sulfoxides such as dimethyl sulfoxide; halogenated hydrocarbons such as dichloromethane, 1,2-dichloroethane, chloroform, carbon tetrachloride and benzotrifluoride; aliphatic hydrocarbons such as pentane, hexane, heptane and octane; aromatic hydrocarbons such as benzene, toluene and xylene; ethers such as diethyl ether, diisopropyl ether, tert-butyl methyl ether, dimethoxyethane, tetrahydrofuran, 1,4-dioxane and 1,3-dioxolane; ketones such as acetone and methyl ethyl ketone; alcohols such as methanol, ethanol, 2-propanol, n-butanol and tert-butanol; polyhydric alcohols such as ethylene glycol, propylene glycol, 1,2-propanediol and glycerol; etc. Each of those solvents may be used alone or as a mixture of two or more thereof. With regards to those solvents, alcohols, etc. are preferred and 2-propanol is more preferred.

Pressure of hydrogen gas may be acceptable if it is under a hydrogen atmosphere and, although 0.1 MPa is sufficient, it will be appropriately selected usually from the range of 0.1 to 20 MPa or, preferably, 0.2 to 10 MPa when economy, etc. are taken into consideration. From economical point of view the pressure of hydrogen gas may be 1 or less MPa.

With regard to reaction temperature, it may be an appropriate temperature from −30° C. to boiling point of the solvent used and, preferably, it is 25° C. to 40° C.

With regard to reaction time, it may be an appropriate time of 1 to 24 hours and, preferably, it is 8 to 20 hours.

The optically active amino alcohol prepared as such is a compound which is very useful as an asymmetric auxiliary group of a compound or an intermediate for production of pharmaceuticals.

The present invention is characterized in that, in the production of an optically active amino alcohol, a keto-enamine which is a compound represented by the above formula (1) is used as a material therefor. The compound represented by the formula (1) is able to give a desired optically active amino alcohol (2) of a high purity and a high optical purity via only one step by means of an asymmetric hydrogenation reaction using an asymmetric metal complex.

As mentioned above, in accordance with the present invention, a desired optically active amino alcohol is prepared in a high yield and a high optical purity and, in addition, working efficiency is improved and more advantage is also resulted in view of economy as compared with the conventional methods.

EXAMPLES

The present invention will now be more specifically illustrated by way of the following Examples although the present invention is not limited thereby at all.

Chemical purity and enantiomer excess were determined by means of a high-performance liquid chromatography.

For $^1$H-NMR, there was used a Varian Gemini-2000 (200 MHe).

Example 1

Production of (1S)-3-(methylamino)-1-(2-thienyl) propan-1-ol

In a nitrogen atmosphere, 3-methylamino-1-thiophen-2-yl-propenone (70 g, 0.418 mol), RuCl$_2$((R)-dm-binap)((R) daipen) (511 mg, 0.41 mmol), potassium carbonate (63.6 g, 0.46 mol) and 2-propanol (700 ml) were added to a one-liter autoclave and, after the air was removed therefrom, hydrogen pressure was charged until a predetermined pressure (2.5 MPa) followed by stirring at 30° C. for 18 hours. Potassium carbonate was removed by filtration and the solvent was evaporated in vacuo. The residue was recrystallized from toluene to give 56.7 g (yield: 79.2%) of (1S)-3-(methylamino)-1-(2-thienyl)propan-1-ol.

Melting point=68 to 70° C. Chemical purity: 99.9%. Optical purity: 99.7% ee.

$^1$H-NMR: (200 MHz): δ (CDCl$_3$) 1.94 (2H, m), 2.44 (3H, s), 2.92 (2H, m), 5.19 (1H, m), 6.94 (2H, m), 7.20 (1H, m)

Example 2

Production of (S)-3-(N-methylamino)-1-phenyl-1-propanol

Into a 100-ml autoclave were charged 500 mg (3.1 mmol) of 3-methylamino-1-phenylpropenone, 7.6 mg (0.062 mmol) of RuCl$_2$[(R)-DM-binap][(R)-daipen] and 88 mg (3.7 mmol) of lithium hydroxide (LiOH), substitution with nitrogen gas was conducted and 5 mL of 2-propanol were added thereto. After substitution with hydrogen gas, the hydrogen pressure was made 3 MPa and stirring was conducted at 30° C. for 17 hours. The reaction solution was filtered through Celite and the filtrate was concentrated to give (S)-3-(N-methylamino)-1-phenyl-1-propanol in a conversion rate of 99% or more and in an optical purity of 98% ee.

$^1$H-NMR (CDCl$_3$) δ 1.72–1.92 (2H, m), 2.44 (3H, s), 2.79–2.93 (2H, m), 4.94 (1H, dd, J=3.3, 8.6 Hz), 7.21–7.39 (5H, m)

INDUSTRIAL APPLICABILITY

In accordance with the present invention, a keto-enamine represented by the formula (1) is used as a material whereby it is now possible that carbonyl group and double bond existing in a molecule are reduced by a simple method in a single step at the same time and that an optically active amino alcohol (2) is prepared in a high yield and in a high optical purity and that is very useful in view of industry.

What is claimed is:

1. A process for producing an optically active amino alcohol represented by the following formula (2)

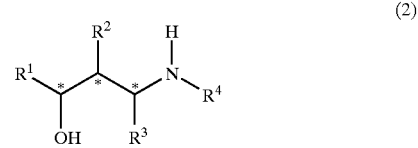

wherein $R^1$ is a hydrocarbon group, a substituted hydrocarbon group, an aromatic heterocyclic group, a substituted aromatic heterocyclic group, an aliphatic heterocyclic group or a substituted aliphatic heterocyclic group; $R^2$ and $R^3$ each independently is hydrogen atom, a hydrocarbon group, a substituted hydrocarbon group, an acyl group, an acyloxy group, an alkyloxycarbonyl group, an aralkyloxycarbonyl group, an aryloxycarbonyl group, an aromatic heterocyclic group, a substituted aromatic heterocyclic group, an aliphatic heterocyclic group or a substituted aliphatic heterocyclic group; $R^4$ hydrogen atom or a protective group; two or more of $R^1$, $R^2$, $R^3$ and $R^4$ may be bonded to each other to form a ring; and * is asymmetric carbon, provided that when $R^2$ or $R^3$ is hydrogen atom, the carbon atom to which $R^2$ or $R^3$ is bonded is not an asymmetric carbon, or a salt thereof, which comprises subjecting a compound represented by the following formula (1) or a salt thereof to an asymmetric hydrogenation reaction in the presence of an asymmetric metal complex wherein formula (1) is:

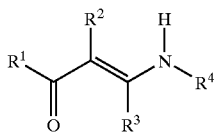 (1)

wherein $R^1$ is a hydrocarbon group, a substituted hydrocarbon group, an aromatic heterocyclic group, a substituted aromatic heterocyclic group, an aliphatic heterocyclic group or a substituted aliphatic heterocyclic group; $R^2$ and $R^3$ each independently is hydrogen atom, a hydrocarbon group, a substituted hydrocarbon group, an acyl group, an acyloxy group, an alkyloxycarbonyl group, an aralkyloxycarbonyl group, an aryloxycarbonyl group, an aromatic heterocyclic group, a substituted aromatic heterocyclic group, an aliphatic heterocyclic group or a substituted aliphatic heterocyclic group; $R^4$ is hydrogen atom or a protective group; two or more of $R^1$, $R^2$, $R^3$ and $R^4$ may be bonded to each other to form a ring; and the double bond between the carbon atoms to which $R^2$ and $R^3$ are attached is cis or trans or a mixture thereof.

2. The process according to claim 1, wherein the asymmetric hydrogenation reaction is carried out in the presence of a base.

3. The process according to claim 2, wherein the amount of the base used is 0.15 to 10 equivalents relative to the compound represented by the formula (1).

4. The process according to claim 1, wherein $R^1$ is a hydrocarbon group, a substituted hydrocarbon group, an aromatic heterocyclic group or a substituted aromatic heterocyclic group, each of $R^2$ and $R^3$ is hydrogen atom and $R^4$ is a protective group.

5. The process according to claim 1, wherein $R^1$ is an aromatic heterocyclic group, a substituted aromatic heterocyclic group, an aryl group or a substituted aryl group, each of $R^2$ and $R^3$ is hydrogen atom and $R^4$ is a hydrocarbon group.

6. The process according to claim 1, wherein $R^1$ is an aromatic heterocyclic group or an aryl group, each of $R^2$ and $R^3$ is hydrogen atom and $R^4$ is an alkyl group.

7. The process according to claim 1, wherein $R^1$ is a thienyl group or a phenyl group, each of $R^2$ and $R^3$ is hydrogen atom and $R^4$ is a methyl group.

8. The process according to claim 1, wherein the compound of formula (2) is (1S)-3-(methylamino)-1-(2-thienyl) propan-1-ol or (S)-3-(N-methylamino)-1-phenyl-1-propanol and the compound of formula (1) is 3-methylamino-1-thiophen-2-yl-propanone or 3-methylamino-1-phenylpropanone.

9. The process according to claim 1, wherein the asymmetric metal complex is $RuCl_2[(R)\text{-binap}][R,R)\text{-dpen}]$, $RuCl_2[(R)\text{-binap}][(R)\text{-daipen}]$, $RuCl_2[(R)\text{-Tol-binap}][(R,R)\text{-dpen}]$, $RuCl_2[(R)\text{-Tol-binap}][(R)\text{-daipen}]$, $RuCl_2[(R)\text{-DM-binap}][R,R)\text{-dpen}]$ or $RuCl_2[(R)\text{-DM-binap}][(R)\text{-daipen}]$, in which binap means 2,2'-bis)diphenylphosphino)-1,1'-binaphthyl, Tol-binap means 2,2'-bis(di-p-tolylphosphino)-1,1'-binaphthyl, DM-binap means 2,2'-bis[bis(3,5-dimethylphenyl)phosphino]-1,1'-binaphthyl, dpen means 1,2-diphenyl-ethylenediamine and daipen means 1,1-di(4-anisyl)-2-isopropyl-1,2-ethylenediamine.

10. The process according to any one of claims 1 or 2 to 9, wherein the asymmetric metal complex is $RuCl_2[(R)\text{-DM-binap}][(R,R)\text{-daipen}]$.

* * * * *

UNITED STATES PATENT AND TRADEMARK OFFICE
CERTIFICATE OF CORRECTION

PATENT NO. : 6,984,738 B2
APPLICATION NO. : 10/686598
DATED : January 10, 2006
INVENTOR(S) : Tohru Yokozawa et al.

It is certified that error appears in the above-identified patent and that said Letters Patent is hereby corrected as shown below:

Column 30,
Lines 16-17, change "3-methylamino-1-thiophen-2-yl-propanone" to
-- 3-methylamino-1-thiophen-2-yl-propenone --;
Lines 17-18, change "3-methylamino-1-phenylpropanone" to
-- 3-methylamino-1-phenylpropenone --;
Line 21, change "RuCl$_2$[(R)-binap][R,R)-dpen]" to
-- RuCl$_2$[(R)-binap][(R,R)-dpen] --;
Lines 23-24, change "RuCl$_2$[(R)-DM-binap][R,R)-dpen]" to
-- RuCl$_2$[(R)-DM-binap][(R,R)-dpen] --;
Lines 25-26, change "2,2'-bis)diphenylphosphino)-1,1'-binaphthyl" to
-- 2,2'-bis(diphenylphosphino)-1,1'-binaphthyl --.

Signed and Sealed this

Eleventh Day of July, 2006

JON W. DUDAS
*Director of the United States Patent and Trademark Office*